US012790489B2

(12) United States Patent
Lucchini et al.

(10) Patent No.: US 12,790,489 B2
(45) Date of Patent: Nov. 10, 2026

(54) METHOD TO PRODUCE A CASEIN-BASED BIOPOLYMER MATRIX FIBER AND THERMAL AND ACOUSTIC INSULATING PANEL MADE WITH SAID FIBER

(71) Applicants: POLITECNICO DI MILANO, Milan (IT); UNIVERSITA' DEGLI STUDI DELLA BASILICATA, Potenza (IT)

(72) Inventors: Angelo Lucchini, Milan (IT); Enrico Sergio Mazzucchelli, Milan (IT); Antonello Pagliuca, Matera (IT); Donato Gallo, Matera (IT)

(73) Assignees: POLITECNICO DI MILANO, Milan (IT); UNIVERSITA' DEGLI STUDI DELLA BASILICATA, Potenza (IT)

( * ) Notice: Subject to any disclaimer, the term of this patent is extended or adjusted under 35 U.S.C. 154(b) by 384 days.

(21) Appl. No.: 18/567,769

(22) PCT Filed: Jun. 7, 2022

(86) PCT No.: PCT/IT2022/050161
§ 371 (c)(1),
(2) Date: Dec. 7, 2023

(87) PCT Pub. No.: WO2022/259278
PCT Pub. Date: Dec. 15, 2022

(65) Prior Publication Data

US 2024/0270966 A1 Aug. 15, 2024

(30) Foreign Application Priority Data

Jun. 8, 2021 (IT) ........................ 102021000014888

(51) Int. Cl.
*C08L 89/00* (2006.01)
*C07K 14/47* (2006.01)
(Continued)

(52) U.S. Cl.
CPC ........ *C08L 89/005* (2013.01); *C07K 14/4732* (2013.01); *E04B 1/90* (2013.01);
(Continued)

(58) Field of Classification Search
None
See application file for complete search history.

(56) References Cited

U.S. PATENT DOCUMENTS 2,204,535 A 6/1940 Gould
2,409,475 A 10/1946 Cline
10,960,096 B2 3/2021 Luthe

FOREIGN PATENT DOCUMENTS

EP 2063040 A2 5/2009

OTHER PUBLICATIONS

Whittier et al "Making Casein Fiber", Industrial and Engineering Chemistry, vol. 32, No. 7, pp. 906-907 (Year: 1940).*
(Continued)

*Primary Examiner* — Stefanie J Cohen
(74) *Attorney, Agent, or Firm* — Kratz, Quintos & Hanson, LLP

(57) ABSTRACT

The invention concerns the production of a rigid or flexible thermal and acoustic insulating panel, made with one or more casein-based biopolymer matrix fibers, thermoset with a reduced percentage of thermoplastic fibers or bio-based and biodegradable binders.

7 Claims, 1 Drawing Sheet

(51) Int. Cl.
*E04B 1/90* (2006.01)
*E04B 1/74* (2006.01)

(52) U.S. Cl.
CPC ....... *C08L 2201/02* (2013.01); *C08L 2205/16* (2013.01); *E04B 2001/743* (2013.01); *E04B 2001/745* (2013.01)

(56) References Cited

OTHER PUBLICATIONS

Textile Coach, Jan. 8, 2021 (Year: 2021).*
International Search Report for International Application No. PCT/IT2022/050161 dated Sep. 29, 2022 (14 sheets).
Whittier, et al.; "Making Casein Fiber"; Industrial & Engineering Chemistry; vol. 32(7); Dec. 31, 1940; pp. 906-907 (2 pages); Retrieved from the Internet: https://pubs.acs.org/doi/pdf/10.1021/ie50367a009?casa_token=fZrfBO3UtAcAAAAA:soZSJswr64Ld1pENysR652tTMfmsffyYxVZgNQR-V7THnyyiGD_AuO1NUV1vuLRippScJUComu-A5eLx1& (retiieved Feb. 28, 2022).

* cited by examiner

METHOD TO PRODUCE A CASEIN-BASED BIOPOLYMER MATRIX FIBER AND THERMAL AND ACOUSTIC INSULATING PANEL MADE WITH SAID FIBER

FIELD OF THE INVENTION

The present invention concerns a method to produce a casein-based biopolymer matrix fiber, produced in loose form and used for the production of a rigid or flexible thermal insulating panel to be applied in the thermal and acoustic insulation sector and for the energy efficiency of the building stock, both historical and new.

BACKGROUND OF THE INVENTION

In the construction sector, thermal and acoustic insulation is an essential requirement for the building trade that is increasingly efficient from an energy-performance point of view and sustainable from an environmental point of view. Both in the energy requalification of the consolidated building stock and in new buildings, the choice of insulating materials is not subordinate exclusively to verifying some technical performance parameters but—for an integrated design—to satisfying requirements in line with the theme of sustainability and environmental compatibility, evaluating the entire life cycle and the environmental impact of the insulating components.

To date, the best-known insulating materials used in the building trade are organic-synthetic and inorganic-synthetic based, such as for example glass wool or rock wool, or polymer materials such as polystyrenes (EPS, XPS), polyurethanes or polyesters. These materials, obtained by petrochemical processes, have a negative environmental balance due to the synthetic nature of their production, the emissions of $CO_2$ into the environment and the large quantity of energy required for production and disposal (as they are non-recyclable/renewable).

Materials of natural origin are also known, as described in document U.S. Pat. No. 10,960,096, which concerns a panel to be integrated into ventilation systems for the absorption of volatile components and pollen, and in which the panel is made with innumerable biodegradable fibers such as: natural fibers (cotton, poplar, bamboo fiber, nettle, hemp, jute, etc.), animal fibers (sheep, alpaca, llama, rabbit, etc.) and protein fibers (soy, collagen, albumin, elastin, chromoproteins, protamines, fibrinogen, etc.). This prior art document contemplates the use of casein as a secondary compound.

These materials of natural origin have the advantage of being eco-sustainable and environmentally friendly, but they have the disadvantage of being subject to biodeterioration and favoring the proliferation of insects, such as moths (tineidae) and dermestids (dermistidae).

In the case of sheeps' wool, the biodeterioration process is due to the presence of the medullary canal containing a horny filament consisting of keratin (fibroin for serigenic animals), the structural protein of the animal fleece. Furthermore, the presence of imbricated scales (cuticle) therein makes it easily alterable in shape and volume, and therefore in both its thermal and mechanical dimensional stability, limiting the possibility of producing composite insulating materials to be applied in specific contexts.

Casein is also an organic protein, present in the milk of mammals in the form of micelles, aggregated together with small regions of calcium phosphate. However, casein fiber lacks a medullary canal similar to that of sheeps' wool. This makes it practically not subject to biodeterioration. Furthermore, casein fiber has a smooth surface, and does not have the cuticles present on the surface of wool fibers. Casein is currently used in the production of natural glues and adhesives, to replace synthetic resins or in the restoration sector for the production of pigmented colors and consolidating packs. In the paper industry it is used as an emulsifier, and in the food sector as a basis for the production of protein-energizing products. In particular, in the construction sector, casein is used in the production of natural mortars, as described in the state of the art.

For example, U.S. Pat. No. 10,960,096 mentions casein as a possible secondary compound, but without providing a concrete example.

Another example is represented by the prior art document FR-A-2942795, which illustrates a type of soundproofing mortar based on cork, vegetable fibers, casein and clay. These last two components act as an adhesive to bind the cork and the vegetable fibers together.

DE-A-19811807 concerns insulating panels consisting of vegetable fibers and water-soluble silicates. The silicates can be cohesive by means of cellulose, derivatives of starch or proteins, such as for example casein.

EP-A-2618998 concerns a fibrous composite panel in which vegetable proteins, coming from soy, sunflower or corn are used, and also animal proteins such as collagen, gelatin, casein, albumin, silk and elastin.

EP-A-2063040 describes a non-combustible thermal and acoustic insulating panel that delays the spread of fires in homes, offices, schools or other buildings for public or private use. The panel is made fireproof by mixing the fibers with a binder such as plaster, lime or cement. The fibers can be natural (like protein fibers such as wool, and vegetable-cellulosic fibers), natural inorganic fibers (asbestos, metals, silicon, glass wool and rock wool), organic synthetic fibers (polyester, polyamide, polyacrylonitrile, polyolefin, polyurethane), inorganic synthetic fibers (carbon fiber) or regenerated organic fibers (rayon, viscose, casein, TVP).

These prior art documents contemplate the use of casein as a binder or as a secondary compound, but not as the main compound of the panel or in the form of fibrous material.

A well-known example of the use of casein for the production of artificial textile fibers is that of Lanital, discovered in 1936 by the Italian chemist Antonio Ferretti and produced by SNIA-Viscosa. In particular, documents U.S. Pat. Nos. 2,338,916 and 2,338,917 respectively describe the methods for making casein-based textile fibers. These fibers have been used exclusively in the textile industry, without any application in the construction sector.

U.S. Pat. No. 2,409,475 and the scientific article by Whittier et al "Making Casein Fiber", identified with the number XP055896083, describe methods for the production of textile fibers similar to Lanital intended for textile manufacturing, without application in the building trade. The characteristics of the fiber described in document U.S. Pat. No. 2,409,475 are improved by a setting process in an acid bath containing formaldehyde (considered highly toxic by the AIRC—Italian Association for Cancer Research), salts and metals (sodium, aluminum, zinc, bromine, chromium, potassium and magnesium).

There is therefore a need to define a method to produce a casein-based biopolymer matrix fiber that can overcome at least one of the disadvantages of the state of the art (environmental incompatibility and toxicity) and that can find an exclusive field of application in the sector of thermal and acoustic insulation of the building stock, both existing and new.

There is also a need to perfect an insulating panel that can overcome at least one of the disadvantages mentioned above.

In particular, one purpose of the present invention is to perfect a method to produce a casein-based biopolymer matrix fiber to be used in the building sector and which has both suitable characteristics of performance (in particular water behavior, rot-proof, fire behavior and mechanical and thermal dimensional stability) and also meets the requirements of environmental sustainability and environmental compatibility.

Another purpose is to provide an insulating panel of casein-based biopolymer matrix fiber which is eco-sustainable and environmentally friendly, and which at the same time provides an optimal level of thermal and acoustic insulation.

Another purpose is to perfect a method that allows to produce a casein-based biopolymer matrix fiber that is not subject to the phenomenon of biodegradation of the macromolecular structure, preserving the mechanical, physical and chemical characteristics and at the same time ensuring biodegradability and recyclability at the end of its useful life cycle.

The Applicant has devised, tested and embodied the present invention to overcome the shortcomings of the state of the art and to obtain these and other purposes and advantages.

SUMMARY OF THE INVENTION

The present invention is set forth and characterized in the independent claims. The dependent claims describe other features of the present invention or variants to the main inventive idea.

In accordance with the above purposes, and in order to resolve the above said technical problem in a new and original way, also achieving considerable advantages with respect to the prior art, a method to produce a casein-based biopolymer matrix fiber comprises a step of solubilizing the casein in a basic solution in aqueous solution, a step of polymerizing the casein in the form of fiber in a first acid solution, and a step of setting the fiber in a second acid solution different from the first acid solution.

The method described above allows to obtain a natural matrix fiber suitable for the formation of a thermal and acoustic insulating panel that has performances comparable to those that can be achieved with wool fibers, the natural insulator most used in the thermal insulation sector. Casein fiber occurs as a linear solid-section polymer. Contrary to wool, casein fiber does not have the medullary canal containing keratin, which allows to drastically reduce the biodegradation process of the new fiber and to improve mechanical and chemical performances.

In accordance with some embodiments, the method can provide an initial step of extracting the casein from milk. This extraction step advantageously comprises a precipitation of the calcium phospho caseinate (casein) by means of acidification or denaturation at the milk's isoelectric point, that is, at pH 4.6.

After the extraction step, and before the dilution step, a washing step can be provided, for example with calcium bicarbonate and dehydrated with a natural drying process at a constant temperature, for example 22° C.

In accordance with some embodiments, the basic solution is produced with an amphoteric metal and preferably a base according to the Arrhenius theory, that is, a base that dissociating in water yields hydroxide ions OH. The base is selected from hydroxides, preferably non-metallic hydroxides, more preferably from ammonium hydroxide, potassium hydroxide and sodium hydroxide.

According to some embodiments, the first acid solution is produced with one or more strong acids, preferably sulfuric acid, possibly mixed with sodium bisulfate. By strong acid it is meant an acid with an acid dissociation constant $pK_a$ lower than −1.74 at 25° C. in water.

Favorably, the second acid solution is based on at least one weak acid, preferably a carboxylic or polycarboxylic acid. By weak acid it is meant an acid with an acid dissociation constant $pK_a$ comprised between −1.74 and 12 at 25° C. in water.

Preferably, the step of solubilizing the casein in basic solution provides a first sub-step of solubilizing the casein in a solution containing a hydroxide, in order to obtain an intermediate basic solution, and subsequently a second sub-step of putting in the presence of the amphoteric metal. This second sub-step can be carried out by mixing the intermediate basic solution in a solution in the presence of the amphoteric metal, or by adding the amphoteric metal into the intermediate basic solution.

The first sub-step of solubilization in the basic solution, which can comprise ammonium hydroxide, potassium hydroxide and/or sodium hydroxide, allows to adjust the orientation of the casein molecules, which thus take on an extended conformation. This sub-step results in a viscous mass of casein which is easily workable, for example to obtain threads or fibers.

The sub-step of putting in the presence of the amphoteric metal, which is preferably copper carbonate, in addition to resulting in a basic solution with a slightly soluble amphoteric metal capable of releasing $OH^-$ ions, also has the function of giving the fiber subsequently produced the due characteristics of mechanical resistance, rot resistance, fire resistance, resistance to the action of microorganisms, toughness and resilience.

At the end of this latter sub-step, a casein product is obtained in the form of viscose, ready for the step of polymerization in an acid solution.

In accordance with some embodiments, the step of polymerization of the casein in order to form a fiber in the first acid solution provides a first sub-step of forming the casein, and a second sub-step of immersion in the first acid solution. Preferably, these two sub-steps are simultaneous, that is, the casein is formed directly within the acid solution. The sub-step of forming can comprise an extrusion of the viscous mass of casein so as to form a fiber.

The forming of the casein, in particular in the form of fiber, directly within the first acid solution allows to perform a linear polymerization, giving rise to the formation of the fiber.

It is advantageous to provide a subsequent sub-step of resting the fiber in the first acid solution, in order to neutralize the part of basic solution extruded together with the fiber.

Finally, this step allows to crosslink the previously obtained fiber, as well as to complete the neutralization of basic substances extruded together with the fiber itself. The crosslinking of the fiber gives it greater mechanical resistance, which makes it suitable for the formation of insulating panels and for the properties of mechanical and thermal dimensional stability. Furthermore, the crosslinking makes the fiber insoluble in water and gives it characteristics of toughness, elasticity and resistance to water and boiling.

The formation of insulating panels can be carried out by means of known methods for forming insulating panels starting from a fiber. For example, a known method for forming insulating panels provides a step of carding, forming and aligning the fibers, and a step of thermo-cohesion or thermosetting, to give dimensional stability to the panel.

Subsequently, the panel obtained is cut to size and packaged.

According to one aspect, there is also provided an insulating panel formed starting from one or more casein-based biopolymer matrix fibers, advantageously obtained by means of the method disclosed above.

According to another aspect, there is provided a use of the casein in the form of fiber to produce a fibrous matrix insulating panel. In this use, the casein fiber is the main component of the panel. Advantageously, the casein fiber is obtained by means of the method as above.

DESCRIPTION OF THE DRAWINGS

These and other aspects, characteristics and advantages of the present invention will become apparent from the following description of some embodiments, given as a non-restrictive example with reference to the attached drawings wherein.

Figure 1:
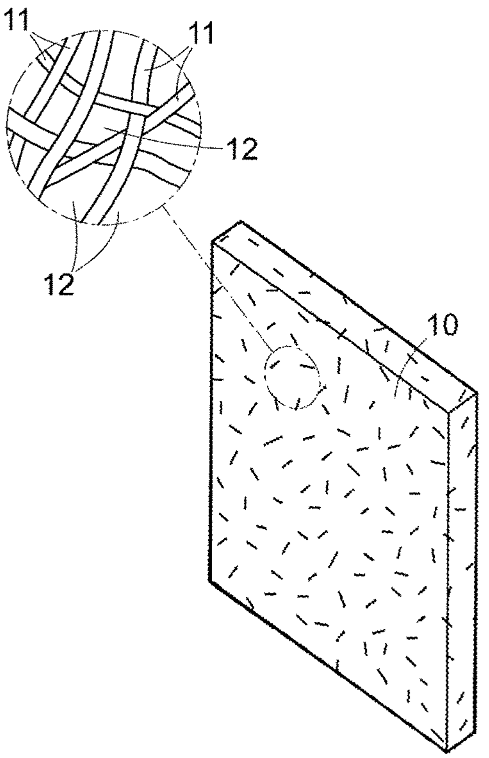
FIG. 1 is a three-dimensional view of a thermoacoustic insulating panel according to the invention.

It is to be clarified that in the present description the phraseology and terminology used, such as for example the terms horizontal, vertical, front, rear, high, low, internal and external, with their declinations, have the sole function of better illustrating the present invention with reference to the attached drawings and must not be in any way used to limit the scope of the invention itself, or the field of protection defined by the attached claims.

Furthermore, the people of skill in the art will recognize that certain sizes or features in the drawings may have been enlarged, deformed, or shown in an unconventional or non-proportional way in order to provide a version of the present invention that is easier to understand. When sizes and/or values are specified in the following description, the sizes and/or values are provided for illustrative purposes only and must not be construed as limiting the scope of protection of the present invention, unless such sizes and/or values are present in the attached claims.

To facilitate comprehension, the same reference numbers have been used, where possible, to identify identical common elements in the drawings. It is understood that elements and features of one embodiment can be conveniently combined incorporated into other embodiments without further clarifications.

DESCRIPTION OF SOME EMBODIMENTS

We will now refer in detail to the possible embodiments of the invention, which are provided by way of a non-limiting example. The phraseology and terminology used here is also for the purposes of providing non-limiting examples.

Unless otherwise defined, all the technical and scientific terms used here and hereafter have the same meaning as commonly understood by a person with ordinary experience in the field of the art to which the present invention belongs.

Even if methods and materials similar or equivalent to those described here can be used in practice and in the trials of the present invention, the methods and materials are described hereafter as an example. In the event of conflict, the present application shall prevail, including its definitions. The materials, methods and examples have a purely illustrative purpose and shall not be understood restrictively.

Unless otherwise indicated, all measurements are carried out at 25° C. (ambient temperature) and at atmospheric pressure. All temperatures are expressed in degrees Celsius, unless otherwise indicated.

All percentages and ratios indicated shall be understood to refer to the weight of the total composition (w/w), unless otherwise indicated.

All the percentage intervals reported here are given with the provision that the sum with respect to the overall composition is 100%, unless otherwise indicated.

All the intervals reported here shall be understood to include the extremes, including those that report an interval "between" two values, unless otherwise indicated.

The present description also includes the intervals that derive from overlapping or uniting two or more intervals described, unless otherwise indicated.

The present description also includes the intervals that can derive from the combination of two or more values taken at different points, unless otherwise indicated.

Where mentioned, water shall be understood to be distilled water, unless otherwise specified.

Embodiments concern a fibrous matrix thermoacoustic insulating panel 1 made up of casein-based biopolymer matrix wool (FIG. 1). The casein fiber 2 has physical and mechanical properties comparable to those of natural wool, although the structural characteristics are different. In fact, while the structure of casein fiber appears as a linear polymer with a solid section (without a medullary canal) and with very regular light streaks, natural wool has a medullary canal consisting of the organic protein keratin. This difference translates into a drastic decrease in the biodegradation process of the casein fiber and a greater durability thereof. This means that the casein fiber produced, while maintaining the grade of eco-sustainable and eco-compatible material as well as performance levels comparable to conventional insulating materials, becomes a valid alternative in the construction sector both to insulating materials made of natural fibers (the commercialization of which is limited by the biodeterioration process as above), and also to materials of synthetic and fossil derivation.

The casein-based biopolymer matrix fiber 2 allows to produce a wool with a density equal to 16.87 kg/m$^3$, a thermal conductivity of 0.035 W/mK, a mechanical strength of 15 kg/mm$^2$, a resistance to steam of 5.14, a toughness of 1.0 g/den when dry and 0.5 g/den when wet, a hygroscopicity value of 120%, an elongation of 60% when dry, an elongation of 40% when wet, a recovery rate of 13.5% and a decomposition temperature of 150° C.

From the point of view of the chemical composition, the casein fiber is made up, with respect to the total weight of the fiber, by weight percentage, of 53% carbon, 7.15% hydrogen, 23% oxygen, 15.30% nitrogen, 0.60% sulfur and 0.95% phosphorus.

The method to obtain the casein-based biopolymer fiber 2, which is used to form the thermal-acoustic insulating panel 1 as above is described below. The fiber 2 constituting the thermoacoustic insulating panel 1 can be produced starting from the recovery of casein from the dairy industry (considered as special waste pursuant to Legislative Decree 5.2.1997, n. 22, pursuant to Article 7), or through the extraction thereof through acidification or denaturation of milk (preferably skimmed milk due to the lower fat content) at its isoelectric point (pH 4.6).

This extraction step (not shown in the drawings) can provide to heat a predetermined quantity of milk, preferably skimmed, to a temperature comprised between 45° C. and 60° C., preferably between 50° C. and 55° C., mixing regularly. Once the desired temperature has been reached, a solution of acetic acid at 28% by weight and with a pH of 4.5 is added, in order to lower the milk's pH to 4.6, which corresponds to its isoelectric point. The volume of acetic acid solution to be added is comprised between 5% and 20% of the milk's volume, preferably between 10% and 15%.

Casein is present in milk in the form of micelles. In the conditions described above, the micelles lose their negative charge and begin to interact with each other, joining and flocculating in order to form a clot with a gelatinous consistency. During this process, Ca ions are expelled, which bind to the lactic acid, salifying and forming calcium lactate. The casein, present in the micelles as calcium phosphocaseinate, loses the calcium and becomes acid phosphocaseinate, which has the form of a clot with a gelatinous consistency (clot).

A syneresis process can then observed, during which the casein precipitates and separates from the residual milk liquid, that is, the whey, which mostly contains lactose, β-lactoglobulin and α-lactalbumin. The syneresis capacity of the clot is mainly linked to the characteristics of elasticity, contractility and permeability, as well as the degree of dehydration of the mass of acid phosphocaseinate. The bonds between the paracasein micelles, the micellar aggregates and the filaments become more and more numerous and strong, causing the contraction of the clot and the consequent expulsion of interstitial water.

A filtration operation is then carried out in order to separate the casein from the whey. The precipitate obtained, which contains casein, is then washed with calcium bicarbonate in order to eliminate the dry substance and to neutralize the acetic acid. The casein is then dehydrated, for example by means of a natural drying process, at a constant temperature of 22° C.

Please note that at an industrial level, it is possible to source casein as a waste product of the dairy industry. In fact, in coagulation by acidification the product of greatest interest is whey, which is used, for example, for the production of butter and derivatives, while casein is usually used in other sectors of the food industry, or for the preparation of adhesives, sheaths and glues in the art restoration sector. It is clear that casein can be a zero cost raw material, easily available, eco-sustainable and eco-compatible, and easy to reuse.

Subsequently, the biopolymer fiber is produced by means of a process of polymerization of the previously obtained casein.

In order to obtain a viscous complex 4 in basic solution, ammonium hydrate in a 23% aqueous solution (or, alternatively, sodium hydroxide) is added to the previously dehydrated casein 5. The viscous complex 4 comes in the form of a yellowish gel with high adhesive capacity. This intermediate product can be used, for example, in the sectors of adhesives, construction and cosmetics.

In the dehydrated state, the casein 5 has a complex molecular structure, and comprises peptide bonds and cross-links which give a coiled or spherical configuration with positively or negatively charged surface groups. In a basic environment, in fact, the casein molecules orient themselves in a regular manner, assuming a linear configuration, giving rise to a viscous mass that can be easily worked and reduced into threads.

Figure 2:
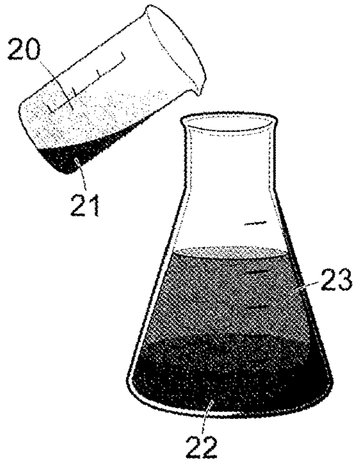
FIGS. 2, 3 and 4 are schematic views of three successive steps of a method to produce a fiber which is the base of the thermoacoustic insulating panel of FIG. 1.

The basic solution 4 of casein 5 is then mixed with an amphoteric metal 6, such as for example copper carbonate, advantageously by means of a magnetic stirrer, for a predetermined amount of time, in order to obtain a basic solution 7 with an intense blue color (FIG. 2). The putting in the presence of ammonia and copper carbonate determines the formation of a copper hydroxide precipitate $Cu(OH)_2$, which subsequently dissolves and forms the tetramine complex $2[Cu(NH_3)_4(H_2O)N]CO_3$ which has a dark blue color. The copper carbonate, therefore, is used for a dual function: the first is to obtain a basic solution through the use of a slightly soluble amphoteric metal such as copper carbonate capable of releasing $OH^-$ ions; the second function is to give the fiber, subsequently produced, the due characteristics of mechanical resistance, rot resistance, fire resistance, toughness and resilience.

It is clarified that, unlike other metals which are difficult to remove, copper carbonate, in the complex form of tetramine-copper (II) can be easily neutralized with a strong acid (e.g. sulfuric acid), making the fiber production process more sustainable throughout the entire life cycle. The use of copper carbonate, compared to other amphoteric metals, gives the final material an additional degree of sustainability. For example, while aluminum hydroxide is obtained by dissolving bauxite in sodium hydroxide at temperatures up to 270° C. (an energy-intensive process), copper carbonate is obtained through a simple precipitation process or through electrolysis, eliminating the use of thermal energy and the consequent production of $CO_2$. This process makes the material particularly sustainable, from an environmental point of view, in its production phase.

In the known methods, the basic solution is made with inorganic substances (e.g. tin silicate, aluminum silicate, tin phosphate) and partly organic substances (e.g. iron tannate) which have a higher solubility and therefore a lower resistance of the fiber. Copper carbonate, on the other hand, overcomes this disadvantage of the state of the art, since it is a poorly soluble amphoteric metal capable of releasing $OH^-$ ions and giving the fiber subsequently produced better characteristics of mechanical resistance.

Copper carbonate is also used in the production of insecticides and fungicides (verdigris, Bordeaux mixture, copper oxychlorides, copper hydroxide, etc.). For this reason, its use—as an alternative to other amphoteric metals used, already known in the state of the art—greatly improves the characteristic of the fiber and of the corresponding insulating panel in resisting the action of microorganisms and fungicidal action. The casein fiber produced, therefore, is rot resistant and resistant to moths. This results, therefore, in the elimination of the mothproof treatment process, which is indispensable, for example, in the case of natural wool in which, in addition to reaching a temperature of 60° C., there is a large consumption of water. Avoiding this treatment, therefore, considerably limits the consumption of water to the advantage of greater sustainability of the finished product.

Furthermore, the absorption of copper carbonate into the body through the air or the skin is insignificant. Numerous other amphoteric metals (such as for example magnesium hydroxide) used for the production of fibrous matrix materials would, on the other hand, be particularly harmful if used in the construction sector.

The fiber produced using copper carbonate has better characteristics of mechanical resistance and, in particular, a better behavior toward water absorption, making the product rot resistant, a fundamental requirement for insulating materials, the performance characteristics of which are particularly sensitive to the actions of humidity.

Figure 3:
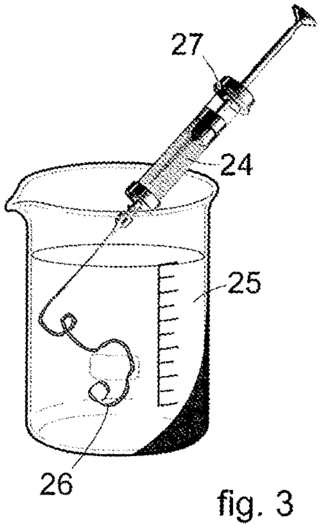

After separation from the hydroxide precipitate $Cu(OH)_2$, a viscous solution 8 is obtained, ready for the next step, in particular of the process of polymerization by extrusion in a coagulating bath 9 (FIG. 3). The extrusion is carried out in a coagulating bath 9 consisting of solutions of sulfuric acid and sodium bisulfate (which is generated automatically since the sodium caseinate, due to the action of the sulfuric acid, breaks down into soluble casein), and allows to obtain a fiber 10 from the process of linear polymerization of the viscous solution of casein into fibrous with crystalline zones (crystallites). In the example shown in FIG. 3, a syringe is used as extruder 11, but it is obviously possible to use any other type of extruder whatsoever, according to production requirements.

The freshly extruded fiber 10 has a blue color that gradually fades, thanks to the action of the sulfuric acid which neutralizes, on the other hand, the alkaline solution of tetramine-copper (II), destroying the complex. The casein fiber 10, therefore, will slowly acquire a yellowish-white color.

Figure 4:
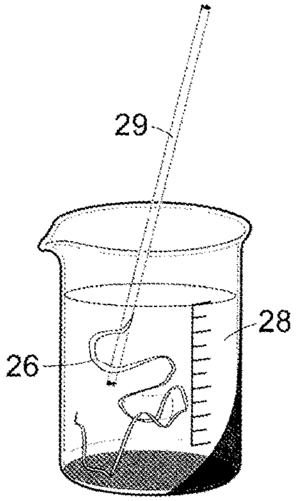

A step of crosslinking the fiber 10 follows, immersing it in a setting bath 12 with the aim of neutralizing the copper carbonate and the ammonia (FIG. 4). The setting bath 12 advantageously contains one or more carboxylic acids or one or more polycarboxylic acids (such as citric acid), as an alternative to the formic acid from which formaldehyde derives. The use of polycarboxylic acids increases the biocompatibility of the fiber obtained. In fact, in the known methods, the step of setting the fiber provides to immerse the fiber in autoclaves, in which it undergoes a treatment at high temperatures with a solution containing formaldehyde (considered highly toxic by the AIRC), zinc sulfate and glucose as a softener. In order to overcome the disadvantage of the state of the art, the setting step is replaced with a crosslinking step, in which the fiber is subjected to a crosslinking bath containing a solution of one or more carboxylic acids or one or more polycarboxylic acids, such as for example citric acid. By polycarboxylic acid is meant an acid comprising two or more carboxylic groups COOH. In this setting step, providing the immersion of the fiber in a solution of one or more carboxylic or polycarboxylic acids, as an alternative to formaldehyde, allows to reduce the production of polluting residues and promote a greater biocompatibility of the fiber in the building sector.

In FIG. 4, the crosslinking step is performed under stirring using a manual stirrer 13, in particular a glass or plastic rod, but it is possible to use other types of stirrers, for example a magnetic stirrer.

In addition, the fiber that until now was soluble in water, due to the polymerizing action of the polycarboxylic acids (or alternatively formaldehyde) acquires the characteristics of toughness, elasticity, resistance to water and to boiling.

Figure 5:
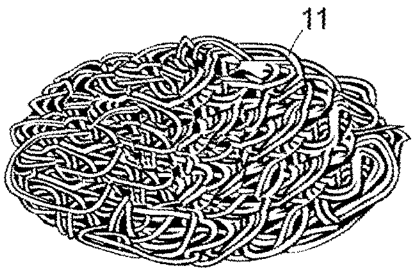
FIG. 5 is a view of a biopolymer fiber obtained through the steps shown in FIGS. 2-4.

After setting, a casein-based fiber 2 of white-yellowish color is obtained (FIG. 5), which can be further whitened by means of known methods.

The casein fiber 2 produced by means of the method described above was subjected to preliminary tests aimed at evaluating its behavior toward fire and water, by means of partial and total immersion tests. It has been verified that when subjected to fire, the fiber obtained burns slowly, leaving a small quantity of carbon residue, a low percentage of smoke and non-existent flammable drops; on the other hand, when the fiber is immersed in water, after 24 hours and after drying, it kept its morphological, dimensional and performance characteristics unaltered.

The casein-based biopolymer matrix fiber 2 thus obtained is the main material for the production of a thermoacoustic insulating panel 1 which can be used in the construction sector.

The morphologically defined formation of the thermoacoustic insulating panel 1 made of casein biopolymer fiber 2 can be carried out by means of known industrial production methods. For example, the production line of the thermoacoustic insulating panel 1 is a machine made up of a series of segments for treating the fiber 2 which perform different functions. The main machines of the line are the former (or pneumatic former) and the air carder, which have the purpose of creating a uniform web of thermoset fibers of variable thickness. The two machines, in fact, can be used independently of each other, depending on the decision on whether to have a thermoacoustic insulating panel with a large or small thickness. Furthermore, the processing through these machines gives the fiber a random order which allows the outgoing web to have an isotropic orientation. The isotropy gives the thermoacoustic insulating panel shape and dimensional stability, and also allows to transmit stresses in different directions (exploiting the intrinsic characteristics of stiffness and resistance) and to create multidirectional load-bearing elements (such as, for example, cladding panels or for false ceilings).

In order to guarantee a low environmental impact of the thermal insulating panel and meet the CAM (Minimum Environmental Criteria)—(Ministerial Decree 11 Oct. 2017), a percentage of recovered or recycled material is used in the production of the panel equal to at least 15% (in terms of weight) of the total of all the materials used. In fact, during production, the thermosetting or thermoforming process (in special thermo-cohesion ovens) is carried out without using resinous substances, but by mixing several fibrous sheets of casein with a reduced percentage (10-15%) of biopolymer-based and biodegradable thermoplastic fibers or binders 3 (such as polylactic acid—PLA, polyhydroxyalkanoates—PHAs, mixtures of vegetable origin such as pectin, cellulose and starch, mixtures of animal origin such as chitin and whey proteins), which are used as an alternative to phenolic urea, amino and melamine resins and are able to make the thermoacoustic insulating panel completely natural and eco-compatible (FIG. 1). Preferably, for the thermo-cohesion step, it is preferable to use biodegradable or non-biodegradable bio-based polymer fibers. Amongst these, polyester fibers are considered fibers from polycondensates, derived from linear polymers formed by a dicarboxylic acid and a divalent alcohol (diol), acting as valid alternatives to phenolic (or formaldehyde), urea, amine and melamine resins.

The use of a percentage of polyester fibers (obtained from the recycling of PET plastics) in the step of thermosetting with the casein fiber allows to be aligned with the environmental ethical principles promulgated by European and international legislation and the certification processes (CE, ETA, ICEA, ANAB, LEED, UNI, ISO, EPD, PEFC, FSC, BREEAM, CasaCinma, EUROCLASSE, EMAS, etc.). These include the CAM which, in the production of insulating materials, introduce the obligation to use a minimum quantity of recycled and/or recovered material. The minimum quantities of recycled content are measured on the weight of the finished product.

Once the thermoacoustic insulating panel 1 has been obtained from the thermo-cohesion process, it is conveyed to special cutting machines for cutting according to established measurements (also into rolls and/or mats), stacked and packaged. The machine also allows to wind the material or to reduce—by means of compression systems—the volume of the roll/panel. Casein fiber, like sheep's wool, can be compressed up to twenty times its original volume. The resulting advantage is a substantial reduction in the space occupied and consequently the number of transport operations necessary for the finished product to reach the place of distribution or installation. The result, therefore, is a reduction in $CO_2$ emissions into the atmosphere caused by transport.

EXAMPLE

A fiber was produced using the method disclosed above, in particular using copper carbonate as an amphoteric metal for the formation of the copper hydroxide precipitate $Cu(OH)_2$. A laboratory test was performed on the fiber thus obtained, in order to calculate long-term water absorption by immersion (UNI EN ISO 16535:2019) and long-term water absorption by diffusion (UNI EN ISO 16536:2019). Long-term water absorption by immersion is determined by measuring the mass of the specimen before and after total immersion for 28 days and it is indicated as volume %. The designation code in technical data sheets and CE labeling is WL(T)i, where "i" is the percentage absorption. For example, WL(T)3 means that the material absorbs a quantity lower than 3% by volume of water. Long-term water absorption by diffusion, on the other hand, indicates the quantity of water that the product is able to absorb when exposed to very high relative humidity (almost 100% on both sides). The designation code in technical data sheets and CE labeling is WD(V)I, where "i" is the percentage absorption. For example, WD(V)5 means that the material absorbs a quantity lower than 5% by volume of water. Finally, the UNI EN ISO 29767:2019 standard defines short-term water absorption by partial immersion and specifies the apparatuses and procedures for terminating short-term water absorption of specimens by means of partial immersion. The designation code in technical data sheets and CE labeling is WS and it is expressed in $Kg/m^2$. Once the test was concluded, the fiber had fully preserved the macromolecular structure and the corresponding properties, confirming the advantage of using copper carbonate as an amphoteric metal. In addition, it was ascertained that the fiber has a hygroscopic behavior very similar to wool, absorbing up to 30% of environmental humidity without appearing wet. The water vapor of the environment, condensing on the fiber, transfers its latent condensation heat to the fiber; therefore, a development of heat occurs in the fiber, which is greater the drier the fiber is. In fact, a moist fiber absorbs less water vapor, and the heat is dispersed by the water already present. This, as well the insulation of the fiber, generates the sense of warmth that is typical of natural wool.

The fiber produced advantageously using copper carbonate has a better fire behavior than those defined according to the state of the art. After a laboratory test, it was noted that the fiber produced does not melt, but decomposes. Since the microstructure of the fiber consists of polymers, it has three temperatures that establish the transition from the amorphous/vitreous state to the viscous/elastic state. In fact, the casein fiber produced burns slowly, releasing a small quantity of carbon residue. Furthermore, according to Ministerial Decree 10 Mar. 2005 and the harmonized standard UNI EN 13501-1:2019, a low percentage of smoke production and the absence of flammable drops produced during the combustion phenomenon were observed.

The fire behavior of the casein fiber was compared with the fire behavior of cotton wool (particularly used in the building sector) and with data obtained from previous tests carried out on Lanital casein fiber. It has been observed that, unlike casein fiber, cotton fiber burns with a stable flame, releasing a smell similar to burnt leaves. In addition, cotton fiber subjected to the action of heat first turns yellow, then takes on a brown color and begins to decompose because of the degradation of the cellulose molecule; finally, it decomposes rapidly, leaving a carbonaceous residue, not too bulky and easily pulverized.

According to "I Georgofili: Atti della R. Accademia dei Georgofili" [Proceedings of the Academy of Georgofili], published by Tipografia M. Ricci 1940, "if one sets fire to Lanital filaments, the flame does not transmit rapidly, as for vegetable fibers (such as cotton), but slowly, obtaining a carbonaceous and spongy residue with the characteristic smell of burnt wool".

Finally, the fire behavior can be further improved by means of a fireproof treatment based on baths of soda, boron salts or other fireproofing additives, including aluminum sulphate.

The casein fiber produced, just like cotton and wool, are quite stable in light; however, with prolonged exposure to sunlight they turn yellow, with a loss of toughness. Furthermore, casein fiber has an important advantage over natural wool and Lanital. In fact, natural wool and Lanital, if stored in airtight places or places with reduced air changes, can exhibit the phenomenon of self-ignition, that is, spontaneous combustion. On the contrary, the casein fiber produced using copper carbonate as an amphoteric metal, given the lower presence of sulfur and fats present on the fiber (which spontaneous oxidation due to effect of atmospheric oxygen depends on), is not subjected to this disadvantage, overcoming one or more problems of the state of the art. This advantage further supports the use of casein fiber in the thermal insulating sector, especially where it is necessary to thermally insulate non-ventilated hollow spaces.

A thermoacoustic insulating panel 1 was produced with the fiber disclosed above, which has a density comprised between 17 and 20 $kg/m^3$, according to the UNI EN ISO 7345:2018 standard, a thermal conductivity equal to 0.035 W/mK, a specific heat of 1450 J/kgK according to the ASTM E 1296 standard, a resistance to vapor diffusion of −5.14% according to the UNI EN ISO 12086 standard, a sound absorption coefficient of 0.65 (able to absorb 65% of the sound wave) and a class E reaction to fire according to the harmonized standard UNI EN 13501-1:2009. These characteristics, partly elaborated in the laboratory, partly obtained from the comparative analysis with natural wool and with the historical fiber Lanital, indicate that the thermoacoustic insulating panel is suitable for application in the thermal and acoustic insulating sector and for improving the energy efficiency of building stocks, both existing and new.

It is clear that multiple densities, sizes and/or shapes can be attributed to the insulating panel, and that modifications and/or additions of parts or steps may be made to the method as described heretofore, without departing from the field and scope of the present invention as defined by the claims.

It is also clear that, although the present invention has been described with reference to some specific examples, a person of skill in the art shall certainly be able to produce many other equivalent forms of packaging methods and plants, having the characteristics as set forth in the claims and hence all coming within the field of protection defined thereby.

The invention claimed is:

1. A method to produce a biopolymer matrix fiber, comprising a step of solubilizing casein in a basic solution in aqueous solution comprising an amphoteric metal and a base selected from hydroxides, a step of polymerizing the casein in a first acid solution in order to form a fiber, and a step of setting said fiber in a second acid solution different from the first acid solution.

2. The method as in claim 1, characterized in that the amphoteric metal is copper carbonate.

3. The method as in claim 1, characterized in that the base is selected from sodium hydroxide and ammonium hydroxide.

4. The method as in claim 1, characterized in that the step of solubilizing the casein in the basic solution comprises a first sub-step of solubilizing the casein in aqueous solution of the base, and a second sub-step of putting in the presence of the amphoteric metal.

5. The method as in claim 1, characterized in that the polymerization step provides a first sub-step of forming the casein, and a second sub-step of immersing the casein in the first acid solution.

6. The method as in claim 5, characterized in that the sub-step of forming and the second sub-step of immersing are simultaneous.

7. The method as in claim 1, characterized in that the step of setting provides a crosslinking of the casein fiber in a solution of one or more of amongst carboxylic acids and polycarboxylic acids.

* * * * *